United States Patent [19]

Shawl et al.

[11] Patent Number: 5,731,476
[45] Date of Patent: *Mar. 24, 1998

[54] POLY ETHER PREPARATION

[75] Inventors: Edward T. Shawl, Wallingford; Haven S. Kesling, Jr., Drexel Hill; Vijai P. Gupta, Berwyn, all of Pa.

[73] Assignee: Arco Chemical Technology, L.P., Greenville, Del.

[*] Notice: The term of this patent shall not extend beyond the expiration date of Pat. No. 5,476,971.

[21] Appl. No.: 566,382

[22] Filed: Dec. 1, 1995

Related U.S. Application Data

[63] Continuation-in-part of Ser. No. 373,672, Jan. 13, 1995, Pat. No. 5,476,971.

[51] Int. Cl.$^6$ .................................................. C07C 43/11
[52] U.S. Cl. .................. 568/619; 568/618; 568/617; 568/613
[58] Field of Search .................................... 568/619, 617, 568/618, 613

[56] References Cited

U.S. PATENT DOCUMENTS

| 1,968,033 | 7/1934 | Evans et al. . |
| 4,270,008 | 5/1981 | Weber et al. . |
| 4,980,511 | 12/1990 | Hoelderich et al. . |
| 5,308,365 | 5/1994 | Kesling et al. . |
| 5,312,995 | 5/1994 | Feraj . |

FOREIGN PATENT DOCUMENTS

| 0282902 | 9/1988 | European Pat. Off. . |
| 0480482 | 4/1992 | European Pat. Off. . |
| 4222183 | 1/1994 | Germany . |
| 2205835 | 12/1988 | United Kingdom . |

*Primary Examiner*—Gary Geist
*Assistant Examiner*—S. Padmanabhan
*Attorney, Agent, or Firm*—Stephen D. Harper; William C. Long

[57] ABSTRACT

Polyethers of polyhydric compounds are prepared by the liquid phase reaction of polyhydric compound and the reaction being carried out with separate liquid phases comprised of a polar polyhydric compound phase and an organic polyether containing phase.

6 Claims, 1 Drawing Sheet

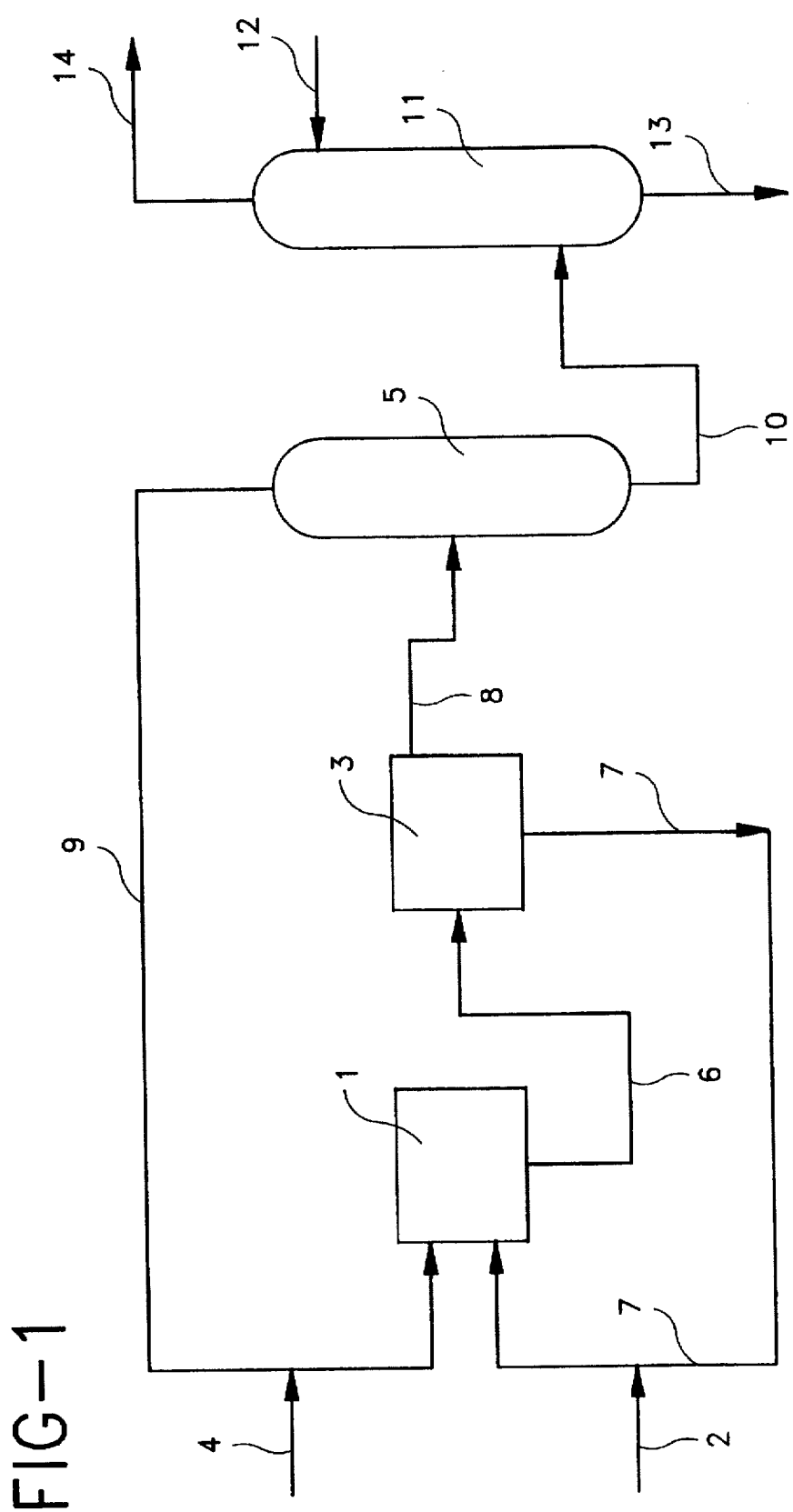

5,731,476

POLY ETHER PREPARATION

BACKGROUND OF THE INVENTION

RELATED APPLICATION

This application is a continuation-in-part of application Ser. No. 08/373,672 filed Jan. 13, 1995, now U.S. Pat. No. 5,476,971.

1. Field of the Invention

The present invention relates to the preparation of poly ethers from polyhydric compounds by reaction of a tertiary olefin having 5–10 carbon atoms or a $C_4$–$C_{10}$ tertiary alkanol or ether derivative thereof with a polyhydric compound in a two phase mode and includes the phase separation of the reaction effluent and recycle of the polar phase which contains unreacted polyhydric compound as well as monoalkyl ether. The invention also relates to the similar preparation of polyethers by reaction of isobutylene with polyhydric compounds having more than 3 hydroxyl groups per molecule.

2. Description of the Prior Art

The preparation of polyol alkyl ethers by reaction of an olefin such as isobutylene with a polyol such as glycerine using an acid catalyst is a known reaction.

U.S. Pat. No. 1,968,033 teaches this reaction using, for example, a sulfuric acid catalyst.

Published German Application No. P 4,222,183.8 teaches this reaction using soluble or insoluble acid catalysts such as p-toluenesulfonic acid, sulfoacetic acid, sulfosuccinic acid, sulfotriacetin, and dodecylbenzenesulfonic acid.

U.S. Pat. No. 5,308,365 teaches this reaction using a highly cross-linked sulfonic acid ion exchange resin such as Amberlyst XN1010 catalyst.

In the processes of the prior art, difficulties have been encountered in the recovery of reaction products from the etherification reaction mixtures, and in the production of particular desired ether products from among the several possible products.

BRIEF DESCRIPTION OF THE INVENTION

In accordance with the present invention, the reaction of the polyhydric compound with the $C_5C_{10}$ tertiary olefin or $C_4$–$C_{10}$ tertiary alkanol or ether derivative or with isobutylene is carried out in the liquid phase in a two phase reaction system, one phase being a polyhydric-rich polar phase and the other phase being an olefin or alkanol or derivative-rich hydrocarbon phase. An acidic catalyst is employed which is primarily contained in the polar phase. The reaction mixture is phase separated into the heavier polyhydric compound and catalyst containing polar phase which is conveniently recycled, and a lighter hydrocarbon phase from which product ethers can be readily separated.

DESCRIPTION OF THE DRAWING

The accompanying drawing illustrates schematically practice of the invention.

DETAILED DESCRIPTION

Referring to the accompanying drawing, there is described therein an embodiment of the invention where glycerine is continuously reacted with isoamylene to form alkyl diether product. The acid catalyzed reaction of glycerine and isoamylene takes place in reaction zone 1 which is, for example, a CSTR, and in which the reactants are maintained in two distinct but well dispersed liquid phases.

Net feed glycerine and make up catalyst as needed are fed via line 2, together with a recycle glycerine phase from decantation zone 3, to reaction zone 1 while net feed isoamylene is fed via line 4, together with recycle isoamylene from stripper 5, to reaction zone 1. It is necessary that the net glycerine and isoamylene fed to zone 1 comprise more than 1 mol preferably up to 2 mols isoamylene per mol of glycerine. More isoamylene can be employed.

The acid catalyst which is employed, e.g. p-toluenesulfonic acid, methane sulfonic acid, and the like, is contained primarily in the glycerine phase in reaction zone 1. The isoamylene and glycerine are substantially immiscible and with suitable agitation form two phases in reaction zone 1, a polar glycerine phase and an isoamylene phase. There is some isoamylene dissolved in the glycerine phase and most of the etherification reaction occurs in this phase. Mass transfer from the isoamylene phase to the glycerine phase maintains the supply of isoamylene in the glycerine phase.

Mono t-amyl glycerine formed in the glycerine phase will mainly remain in this phase. However, di-t-amyl glycerine product will preferentially transfer to the isoamylene phase. Because the great bulk of the catalytic etherification takes place in the glycerine phase, there is a substantially reduced tendency for di-t-amyl glycerine to further react to form the less desirable tri-t-amyl glycerine.

The reaction mixture is removed from reaction zone 1 and passes via line 6 to decantation zone 3 where it separates into an upper isoamylene phase comprised of mono-t-amyl glycerine, di-tamyl glycerine and tri-t-amyl glycerine in addition to the unreacted isoamylene, and a lower glycerine phase comprised of glycerine, mono-t-amyl glycerine, catalyst and small amounts of di- and tri-t-amyl glycerine.

The glycerine phase passes via line 7 back to reaction zone 1 together with net feed glycerine and make up catalyst. The isoamylene phase passes from decantation zone 3 via line 8 to stripping column 5 wherein unreacted isoamylene is stripped overhead and passes via line 9 back to reaction zone 1 along with net feed isoamylene.

The bottoms stream from stripper 5 comprises a small amount of catalyst, glycerine and mono-t-amyl glycerine as well as the di-t-amyl glycerine and tri-t-amyl glycerine products. This bottoms stream passes via line 10 to water wash column 11 wherein it is contacted with water which is introduced via line 12. Glycerine, catalyst and mono-t-amyl glycerine are extracted in the water and are removed via line 13 for recovery or disposal. This stream can be recycled to reaction zone 1 after water removal (not shown).

Product di-t-amyl glycerine together with such tri-t-amyl glycerine as is formed in reaction zone 1 is recovered via line 14.

A special advantage of the invention is that distillation of the high boiling glycerine and glycerine ethers can be avoided. Another advantage is that the less desirable mono-t-amyl ether product is conveniently separated and recycled to the reaction zone for conversion to the more valuable di-t-amyl ether while the further reaction of di-t-amyl glycerine to the tri-t-amyl ether is substantially suppressed. The di-t-amyl glycerine produced in accordance with the invention is a mixture of predominantly 1,3 di-t-amyl glycerine together with lesser amounts of 1,2 di-t-amyl glycerine.

Polyhydric compounds which are converted to ether derivatives in accordance with the invention are those having at least 3 primary or secondary hydroxyl groups, preferably those having 3 hydroxyl groups up to about 5 hydroxyl groups per molecule. Illustrative polyhydric compounds include glycerine, erythritol, pentaerythritol, mannitol, sorbitol, 1,2,6-hexanetriol, 1,2,4-butanetriol, 1,1,1-tris (hydroxymethyl) ethane, 2-ethyl-2 (hydroxymethyl)-1,3-propanediol, as well as oxyalkylated derivatives of the formula

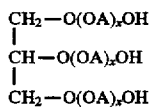

wherein A is —CH$_2$—CH$_2$—O—,

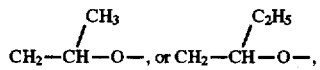

and x is 1–20. Especially preferred as those derivatives where A is

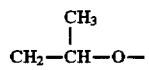

and x is 1–3 and the like.

In accordance with the invention, the polyhydric compound is reacted with a $C_5$–$C_{10}$ tertiary olefin or with a $C_4$–$C_{10}$ tertiary alkanol or ether derivative or with isobutylene in the case of polyhydric compounds having more than 3 hydroxyl groups per molecule to form product polyether.

Illustrative $C_5$–$C_{10}$ tertiary olefin reactants are isoamylene, 1-methyl cyclohexene, alpha methyl styrene, 2,3-dimethyl butene -2, diisobutylene, 2,3,4-trimethyl-2-pentene, and the like.

Illustrative $C_4$–$C_{10}$ tertiary alkanols are t-butanol, t-amyl alcohol, methyl cyclohexan-1-ol, diisobutylene alcohol, and the like as well as ether derivatives thereof.

Several embodiments of the invention can readily be practiced. In an embodiment especially applicable to systems where the polyhydric compound is reacted with a relatively polar reagent such as t-butanol or t-amyl alcohol, an inert non-polar solvent such as pentane, hexane or the like is employed. The use of such a solvent is thought to aid in maintaining two phases during the reaction and in the phase separation. The use of a non-polar solvent is not necessary where a $C_5$–$C_{10}$ tertiary olefin is reacted, but should be used with the polar reactants especially the lower tertiary alkanols, i.e. those having 4 to 6 carbon atoms. Generally $C_5$–$C_{12}$ saturated or aromatic hydrocarbons are preferred non-polar solvents.

As above indicated, it is preferred that the feed to the etherification comprise at least one mol up to two mols of olefin, tertiary alkanol or ether derivative per mol of polyhydric reactant.

It is also important that the reaction mixture in the etherification zone be maintained such that the polar phase comprises at least 30 wt % of the total reaction mixture, and that the polyhydric compound content of the polar phase comprise at least 50 wt % and preferably at least 60 wt % of the polar phase.

The use of water as an additive to increase the polar nature of the polyhydric phase is useful, especially with the higher, less polar alkanol reactants.

Reaction conditions which are employed for the etherification are temperatures of about 40°–150° C., preferably about 50°–100° C. Pressures are sufficient to maintain the liquid phase, e.g. about 30 to 300 psig. Catalyst is employed in amounts of about 0.1 to 5.0 wt % of the reaction mixture, preferably about 0.5 to 2.5%.

The following examples illustrate practice of the invention.

EXAMPLE 1

Referring to the accompanying drawing, isoamylene is continuously reacted with glycerine to form di-t-amyl glycerine product which is primarily 1,3 di-tertiary amyl glycerine.

About 51 lbs/hr of net glycerine feed is fed via line 2 to reaction zone 1 together with the recycle polar phase from decantation zone 3. About 58 lbs/hr of isoamylene is fed to zone 1 via line 4 together with a recycle hydrocarbon mixture from stripper 5.

Reactor 1 is a well agitated continuously stirred tank reactor, reaction conditions are maintained at 60° C. and 100 psig.

Residence time in reactor 1 is about 2.5 hours.

About 260 lbs/hr of liquid reaction mixture passes from reactor 1 via line 6 to decantation zone where the reaction mixture phase separates into a lower polar glycerine phase and an upper organic hydrocarbon phase. The lower glycerine phase has a composition by weight of 65% glycerine, 30% mono-tertiary amyl glycerine, and 2% para-toluene sulfonic acid, and this phase is recycled via line 7 to reactor 1 at the rate of 96 lbs/hr.

The upper organic phase passes at the rate of 164 lbs/hr to stripper 5 wherein 55 tbs/hr isoamylene is stripped overhead and recycled via line 9 to reactor 1.

A bottom stream comprised by weight of 53% di-tertiary amyl glycerine, 44% mono-tertiary amyl glycerine, 15% tri-tertiary amyl glycerine, 1.5% glycerine and a trace of para-toluene sulfonic acid passes at the rate of 109 lbs/hr to extraction zone 11. Water is introduced into zone 11 via line 12 at the rate of 50 lbs/hr and countercurrently extracts glycerine, catalyst and mono-tertiary amyl glycerine and is removed via line 13 at the rate of 95 lbs/hr for disposal or recovery of the various components.

The organic phase is recovered from zone 11 via line 14 at the rate of 64 lbs/hr. This product stream comprises a trace of mono-tertiary amyl glycerine and 97% di-tertiary amyl glycerine and 3% tri-tertiary amyl glycerine, by weight.

As can be seen from the above, practice of the invention provides the means for selective production of the valuable di-tertiary alkyl glycerine while suppressing formation of the less desirable tri-tertiary alkyl glycerine.

EXAMPLE 2

A mixture of 233 g glycerol (2.3 mole), 129 g t-butyl alcohol (1.7 mole), 130 g pentane, and 2.5 methane sulfonic acid (0.03 mole) was charged to a 1 liter autoclave and heated under autogeneous pressure to 90° C. for 3 hours. The phases were separated and analyzed. The conversion of glycerol was 12%, overall selectivities based on glycerol were 49% to mono-t-butyl glycerol, 50% to di-t-butyl glycerol and 0.1% to tri-t-butyl ether. However, 75% of the mono-ether remained in the glycerol phase for recycle so that the distribution of products isolated from the hydrocarbon phase was 82% di-t-butyl ether, 14% mono-t-butyl ether and 4% tri-t-butyl ether by weight.

EXAMPLE 3

A mixture of 2500 g glycerin, 2500 g n-hexane, 1200 g t-amyl alcohol and 45 g methane sulfonic acid were charged to a 5 gallon pressure vessel reactor. The mixture was heated to 80° C. and maintained at this temperature for 5 hours under agitation and at autogenous pressure.

The mixture was cooled, and the phases were separated and analyzed.

Di-t-amyl ether product was primarily contained in the hexane phase, molar yield based on t-butyl alcohol charged was about 4%. The weight ratio of monoether to diether formed was about 1 to 13.

The use of more acidic catalysts and higher reaction temperatures results in increased diether yields.

We claim:

1. In a process for the preparation of a polyether by reaction of a polyhydric compound having at least 3 hydroxyl groups per molecule with a $C_5$–$C_{10}$ tertiary olefin or a $C_4$–$C_{10}$ tertiary alkanol or ether, or by reaction of isobutylene with a polyhydric compound having more than 3 hydroxyl groups per molecule in the presence of an acid catalyst the improvement which comprises carrying out the reaction in the liquid phase while maintaining separate phases comprised of a polar polyhydric compound phase and a hydrocarbon phase.

2. The process of claim 1 wherein the polar phase comprises at least 30% by weight of the reaction mixture.

3. The process of claim 1 wherein the polar phase is comprised of at least 50 wt % polyhydric compound.

4. The process of claim 1 wherein the polar phase is comprised of at least 60 wt % polyhydric compound.

5. In a process for the preparation of di-t-butyl glycerine by reaction of t-butanol with glycerine in the presence of an acid catalyst the improvement which comprises carrying out the reaction in the liquid phase with a hydrocarbon solvent while maintaining separate phases comprised of a polar glycerine phase and a hydrocarbon solvent phase and recovering product di-t-butyl glycerine from the hydrocarbon solvent phase.

6. In a process for the preparation of di-t-amyl glycerine by reaction of tertiary amylene with glycerine in the presence of an acid catalyst the improvement which comprises carrying out the reaction in the liquid phase while maintaining separate phases comprised of a polar glycerine phase and a t-amylene phase and recovering product di-t-amyl glycerine from the t-amylene phase.

* * * * *